US00PP25422P2

(12) United States Plant Patent
Hartman

(10) Patent No.: US PP25,422 P2
(45) Date of Patent: Apr. 7, 2015

(54) ***CALADIUM* PLANT NAMED 'WHITE MAJESTY'**

(50) Latin Name: *Caladium×hortulanum*
Varietal Denomination: White Majesty

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 141 days.

(21) Appl. No.: 13/986,551

(22) Filed: May 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'White Majesty', characterized by its upright and uniformly mounding plant habit; vigorous growth habit and rapid growth rate; large and broad lance-type leaves that are medium green in color with white and greyed green-colored centers and venation; and good landscape performance.

3 Drawing Sheets

Botanical designation: *Caladium×hortulanum.*
Cultivar denomination: 'WHITE MAJESTY'.

BACKGROUND OF THE INVENTION

The present invention relates to a new and distinct cultivar of *Caladium* plant, botanically known as *Caladium×hortulanum*, commercially referred to as a lance (strap) leaf-type *Caladium* and hereinafter referred to by the name 'White Majesty'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2006 in Avon Park, Fla. of a proprietary selection of *Caladium×hortulanum* identified as code number WS-02-18, not patented, as the female, or seed, parent with *Caladium×hortulanum* 'Victoria', disclosed in U.S. Plant Pat. No. 18,087, as the male, or pollen, parent. The new *Caladium* plant was discovered and selected by the Inventor as a single plant within the progeny of the stated cross-pollination in a controlled outdoor nursery environment in Zolfo Springs, Fla. on September, 2007.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2008 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'White Majesty'. These characteristics in combination distinguish 'White Majesty' as a new and distinct *Caladium* plant:

1. Upright and uniformly mounding plant habit.
2. Vigorous growth habit and rapid growth rate.
3. Large and broad lance-type leaves that are medium green in color with white and greyed green-colored centers and venation.
4. Good landscape performance.

Plants of the new *Caladium* differ primarily from plants of the female parent selection in the following characteristics:

1. Plants of the new *Caladium* are taller and more upright than plants of the female parent selection.
2. Plants of the new *Caladium* and the female parent selection differ in leaf shape color as plants of the female parent selection have narrower leaves that are white and greyed white in color with a faint pink-colored blush and green-colored margins.
3. Plants of the new *Caladium* and the female parent selection differ in leaf petiole color as plants of the female parent selection have green-colored leaf petioles with dark green-colored stippling and streaks.

Plants of the new *Caladium* differ primarily from plants of the male parent, 'Victoria', in the following characteristics:

1. Plants of the new *Caladium* are taller and more upright than plants of 'Victoria'.
2. Plants of the new *Caladium* and 'Victoria' differ in leaf shape and coloration as plants of 'Victoria' have narrower undulate leaves that are greyed green in color and overlain with pink with rose red-colored venation and green-colored margins.
3. Plants of the *Caladium* and 'Victoria' differ in leaf petiole coloration as leaf petioles of plants of 'Victoria' are tan pink in color with darker-colored stripes.

Plants of the new *Caladium* can be compared to plants of *Caladium×hortulanum* 'White Star', not patented. In side-by-side comparisons, plants of the new *Caladium* differed primarily from plants of 'White Star' in the following characteristics:

1. Plants of the new *Caladium* were taller than plants of 'White Star'.
2. Plants of the new *Caladium* grew slower than plants of 'White Star' as plants of the new *Caladium* produced finished plants about one to two weeks later than plants of 'White Star'.
3. Plants of the new *Caladium* and 'White Star' differed in leaf shape and coloration as leaves of plants of 'White Star' were narrower, more undulate and green in color with white to grey green-colored centers, pink to light pink-colored venation and dark green-colored margins.
4. Plants of the new *Caladium* and 'White Star' differed in leaf petiole coloration as leaf petioles of plants of 'White Star' were tan pink with darker-colored stippling.

Plants of the new *Caladium* can be compared to plants of *Caladium×hortulanum* 'White Wing', not patented. In side-by-side comparisons, plants of the new *Caladium* differed primarily from plants of 'White Wing' in the following characteristics:

1. Plants of the new *Caladium* and 'White Wing' differed in leaf shape and coloration as plants of 'White Wing' had narrower undulate leaves that were dark green in color with creamy white-colored centers and variably mottled margins.
2. Plants of the new *Caladium* and 'White Wing' differed in leaf petiole coloration as leaf petioles of plants of 'White Wing' were tan pink to green in color with darker-colored stippling.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'White Majesty' in a 15-cm container and grown in a shadehouse.

The photograph at the top of the second sheet is a view of typical plants of 'White Majesty' grown in an open field.

The photograph at the bottom of the second sheet is a close-up view of typical freshly-harvested tubers and roots of 'White Majesty'.

The photograph at the top of the third sheet is a comparison view of typical potted plants of the female parent selection (left), 'White Majesty' (center) and the male parent, 'Victoria' (right).

The photograph at the bottom of the third sheet is a comparison view of typical potted plants of 'White Star' (left), 'White Majesty' (center) and 'White Wing' (right).

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds in an outdoor nursery in Crewsville, Fla. The plants were grown under cultural practices typical of commercial shadehouse and outdoor nursery production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'White Majesty'.

Parentage:

*Female, or seed, parent.*—Proprietary selection of *Caladium×hortulanum* identified as code number 'WS-02-18', not patented.

*Male, or pollen, parent.*—*Caladium×hortulanum* 'Victoria', disclosed in U.S. Plant Pat. No. 18,087.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented and somewhat flattened; individual segments ovate in shape. Height: About 3 cm. Diameter: About 3.8 cm. Segment height: About 1.9 cm. Segment diameter: About 1.5 cm to 2 cm. Texture: Thick, starchy; somewhat brittle. Color: Epidermis, freshly-harvested: Close to N170D and 36D. Epidermis, dried: Close to 200A to 200B. Cortical tissue: Close to 158D. Axillary buds: Close to 36C and 27C. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Upright and uniformly mounding plant habit; vigorous and dense growth habit; rapid growth rate, potted plants in finished or saleable form in about eight weeks after planting tubers; leaf petioles and leaves arise from one or more growing points on tubers; petioles mostly upright and arching outwardly with development.

*Plant height, from soil level to top of foliar plane, shadehouse-grown potted plants.*—About 28 cm to 35 cm.

*Plant diameter or spread, shadehouse-grown potted plants.*—About 53 cm to 57 cm.

*Number of clumps per plant, shadehouse-grown potted plants.*—About three to four from de-eyed tubers.

*Cataphylls, shadehouse-grown potted plants.*—Length: About 6.2 cm to 8 cm. Width: About 1.2 cm. Shape: Wedge-shaped to ovate. Apex: Acute. Base: Sheathing the stem. Color, outer surface: Close to N170D tinged with close to 182D and stippled and streaked with close to 200B tinged with close to 147B; with development, color becoming closer to 200C and N199B faintly stained with close to N186D. Color, inner surface: Close to N155C; outer surface colors and patterns visible.

Foliage description:

*Arrangement and type*.—Alternate; simple; lance-type.

*Length, shadehouse-grown potted plants*.—About 19.3 cm to 23 cm.

*Width, shadehouse-grown potted plants, flattened*.—About 11.7 cm to 15.5 cm.

*Shape*.—Ovate.

*Apex*.—Acuminate.

*Base*.—Sagittate, peltate or obtuse.

*Margin*.—Entire; with broad undulations.

*Texture, upper surface*.—Smooth, glabrous; leathery; dull sheen.

*Texture, lower surface*.—Smooth, glabrous; glaucous.

*Venation pattern*.—Pinnate.

*Color, shadehouse-grown potted plants*.—Developing leaves, upper surface: Background color: Close to 147A tinged with close to N189A; center, close to 155C, 190B and 191C; margin, close to 187B. Basal notch: Close to 187A and 187B. Venation: Close to 191C and 190B. Developing leaves, lower surface: Background color: Close to 191A variably tinged with close to N187A; center, close to 155C; margin, close to 187B. Basal notch: Close to 187A. Midvein: Close to 147B to 147C and 191A tinged with close to 182D. Primary venation: Close to 191A and 147B to 147C. Fully expanded leaves, upper surface: Background color: Close to 147A; center, close to 137B; 147B, 155A and 191C to 191D; margin, close to 187B. Basal notch: Close to 187A and 187B to 187C. Midvein: Close to 156C to 156D distally tinged with close to 191D. Primary venation: Close to 156C to 156D. Fully expanded leaves, lower surface: Background color: Close to 191A and 189A variably tinged with close to N187A; center, close to 147B, 147C and 155A; margin, close to 187B. Basal notch: Close to 187A. Midvein: Close to 147B to 147C and 191A tinged with close to 182D. Primary venation: Close to 146C.

*Petiole*.—Aspect: Initially upright and straight; with development, leaning outwardly; flexible. Length, shadehouse-grown potted plants: About 26 cm to 32 cm. Diameter, distal, shadehouse-grown potted plants: About 4 mm to 5.5 mm. Diameter, proximal, shadehouse-grown potted plants: About 7 mm to 10 mm. Color, shadehouse-grown potted plants: Just below the leaf and petiole junction close to 147B to 147C often tinged with close to 182D and variably streaked or striped with close to 200A to 200B; overall, close to 200A to 200B variably striped with close to N170D and 182D and stippled and tessellated with close to 200A tinged with close to 147B. Wing length, shadehouse-grown potted plants: About 5.5 cm to 7 cm. Wing diameter, shadehouse-grown potted plants: About 7 mm to 10 mm. Wing color, shadehouse-grown potted plants, outer surface: Close to N170D tinged with close to 182D and stippled, streaked and marbled with close to 200A to 200B tinged with close to 147B. Wing color, shadehouse-grown potted plants, inner surface: Close to N155C; outer surface colors and patterns visible.

Inflorescence description: Inflorescence development has not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'White Majesty' as illustrated and described.

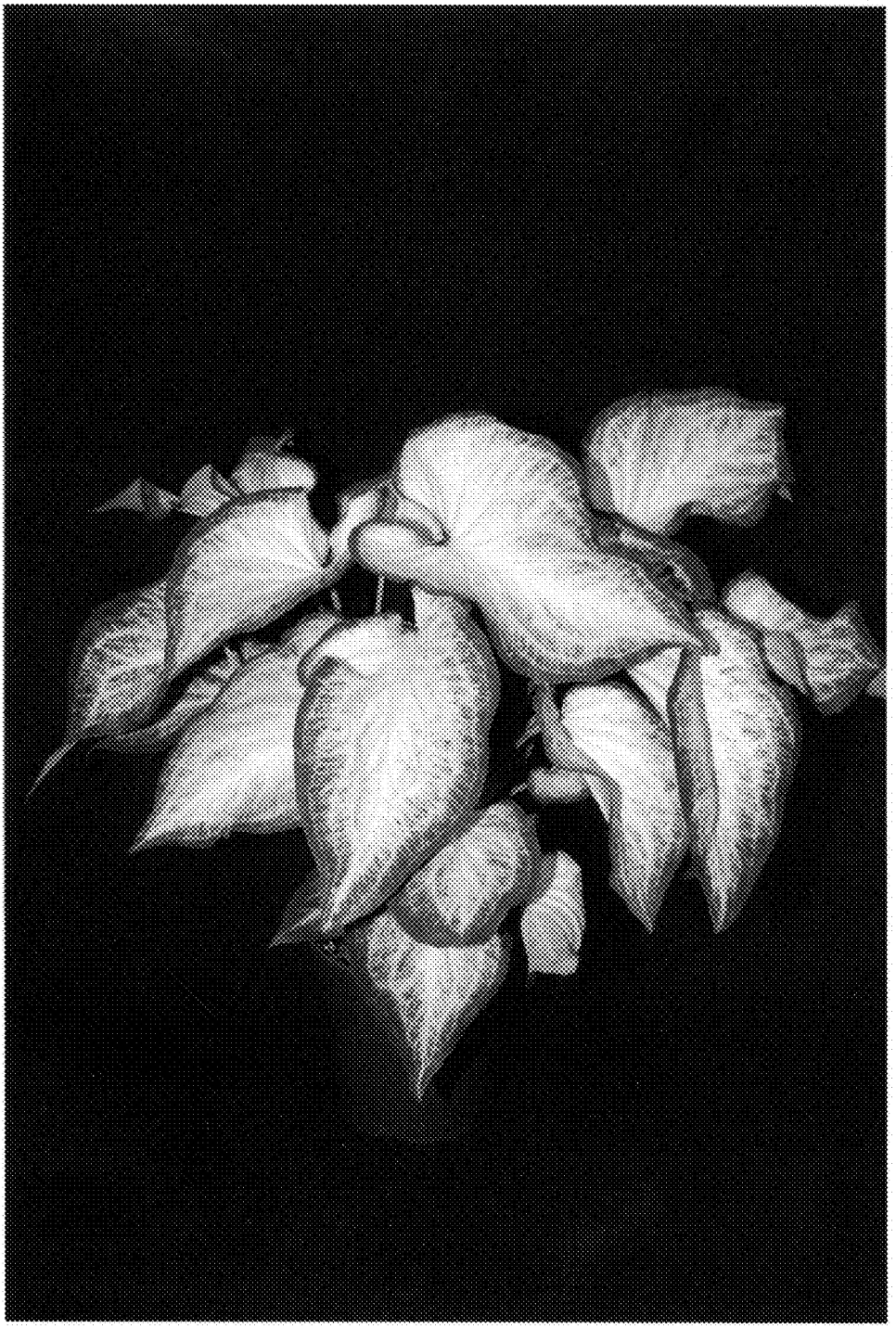

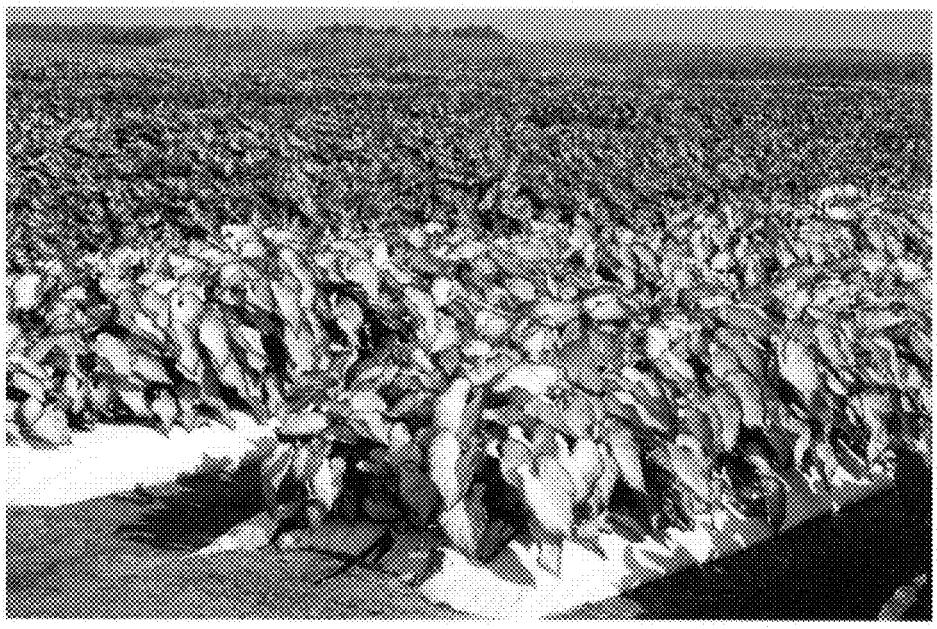
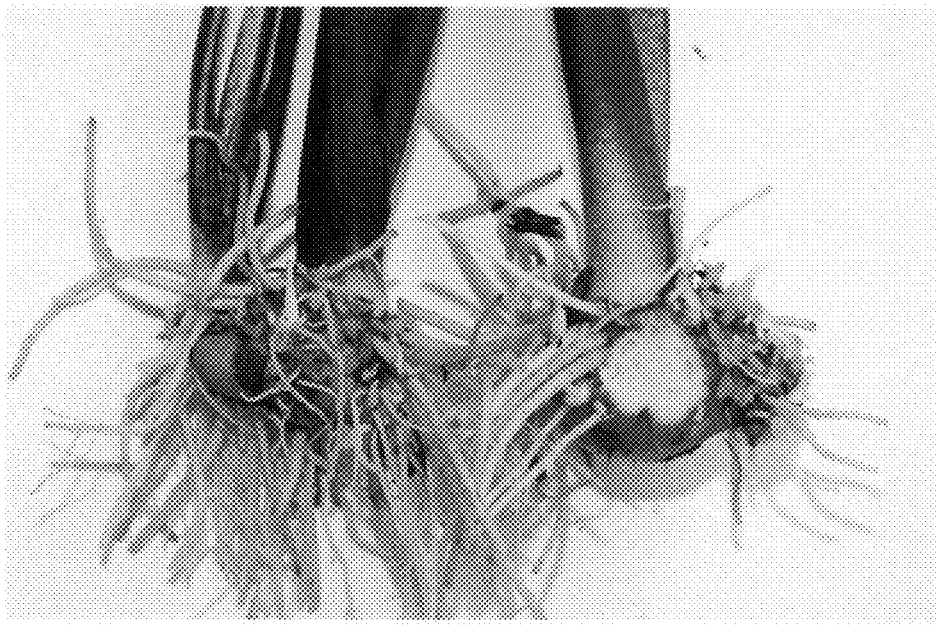

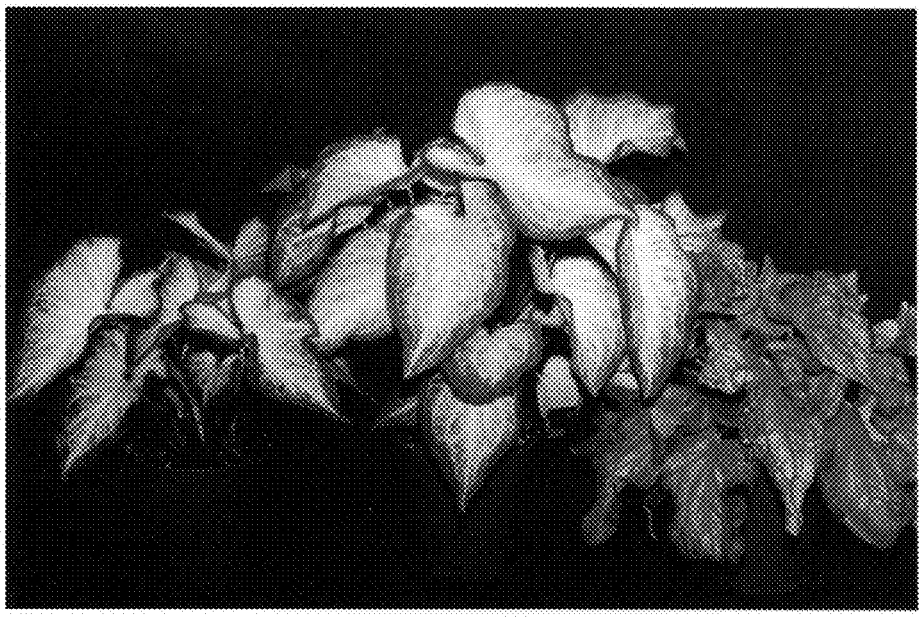
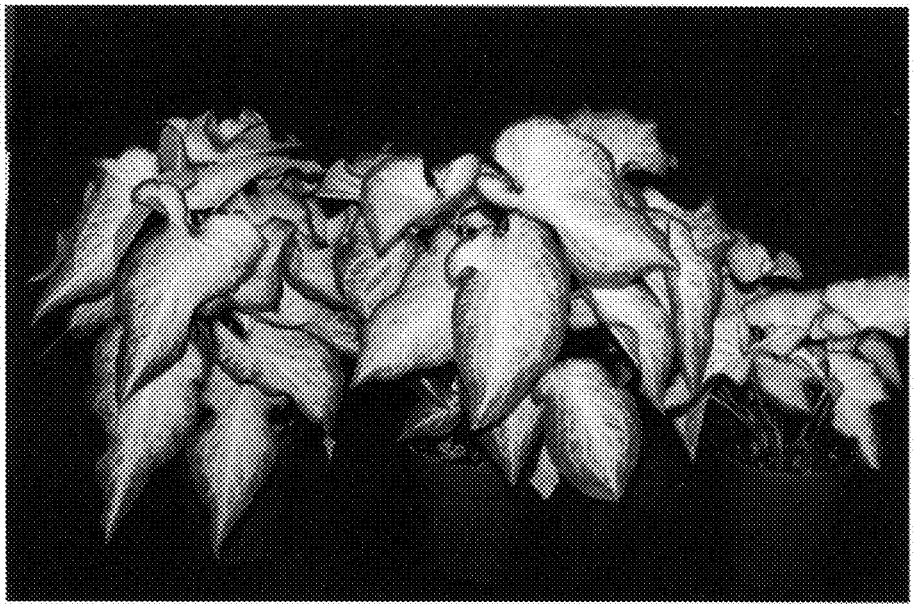

* * * * *